United States Patent
Gross

(10) Patent No.: US 8,866,477 B2
(45) Date of Patent: Oct. 21, 2014

(54) MAGNETIC RESONANCE METHOD AND SYSTEM FOR PHASE CORRECTION OF MAGNETIC RESONANCE SIGNALS ORIGINATING IN MIXED TISSUE

(75) Inventor: Patrick Gross, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 420 days.

(21) Appl. No.: 13/302,251

(22) Filed: Nov. 22, 2011

(65) Prior Publication Data

US 2012/0133362 A1 May 31, 2012

(30) Foreign Application Priority Data

Nov. 25, 2010 (DE) .................... 10 2010 061 974

(51) Int. Cl.
- *G01R 33/54* (2006.01)
- *A61B 5/055* (2006.01)
- *A61B 5/00* (2006.01)
- *A61B 5/01* (2006.01)
- *G01R 33/48* (2006.01)
- *G01R 33/565* (2006.01)

(52) U.S. Cl.
CPC ...... *G01R 33/4804* (2013.01); *G01R 33/56536* (2013.01); *A61B 5/055* (2013.01); *A61B 5/4848* (2013.01); *G01R 33/56563* (2013.01); *A61B 5/01* (2013.01); *G01R 33/4828* (2013.01)
USPC ........................................................ 324/309

(58) Field of Classification Search
CPC ...... G01R 33/54; G01R 33/56; G01R 33/565; G01V 3/00
USPC .................................. 324/300–322
See application file for complete search history.

(56) References Cited

U.S. PATENT DOCUMENTS

| 4,651,098 A * | 3/1987 | Yamada et al. ........... 324/309 |
| 6,428,477 B1 * | 8/2002 | Mason ..................... 600/437 |
| 6,466,016 B1 * | 10/2002 | Miyoshi ................... 324/312 |
| 7,633,293 B2 * | 12/2009 | Olson et al. ............... 324/318 |
| 7,800,368 B2 * | 9/2010 | Vaughan et al. ........... 324/318 |
| 8,115,486 B2 * | 2/2012 | Habara et al. ............. 324/318 |
| 2010/0052674 A1 | 3/2010 | Jellus et al. |
| 2011/0176714 A1 | 7/2011 | Salomir et al. |

FOREIGN PATENT DOCUMENTS

CN 101507603 A 8/2009

OTHER PUBLICATIONS

Rieke, et al: "Referenceless MR Thermometry for Monitoring Thermal Ablation in the Prostate", IEEE Transactions on Medical Imaging, vol. 26, No. 6, Jun. 2007, pp. 813-821.

(Continued)

*Primary Examiner* — Dixomara Vargas
(74) *Attorney, Agent, or Firm* — Schiff Hardin LLP

(57) ABSTRACT

In a magnetic resonance (MR) system and method to separate an MR system-dependent phase influence from a subject-dependent phase influence in phase values of an MR phase image data set of an examination subject, to which two different tissue types with different resonance frequencies make a signal contribution, the system-dependent phase influence is determined by selecting a contour around a region shown in the MR phase image data set, calculating the system-dependent phase influence in this region with the assumption that the spatial curve of the background phase corresponds to a harmonic or quasi-harmonic function, and subtracting the system-dependent phase influence from the acquired phase image data set to determine the subject-dependent phase influence.

9 Claims, 5 Drawing Sheets

(56) References Cited

OTHER PUBLICATIONS

Koktzoglou et al: "Dephased FLAPS for improved visualization of susceptibility-shifted passive devices for real-time interventional MRI", Phys. Med. Biol. vol. 52 (2007), pp. N277-N286.

Bakker et al: "Dephased MRI", Magn. Reson. Med. 55 (2006), pp. 92-97.

Rieke et al. "MR thermometry", J. Magn. Res. Imag. 27 (2008), pp. 376-390.

Grissom et al: "Reweighted $I_1$ Referenceless PRF Shift Thermometry", in Magn Reson Med, vol. 64 (2010), pp. 1068-1077.

Li et al: "An Internal Reference Model-Based PRF Temperature Mapping Method With Cramer-Rap Lower Bound Noise Performance Analysis", Magnetic Resonance in Medicine vol. 62, pp. 1251-1260, (2009).

Sprinkhuizen et al., Temperature-Induced Tissue Susceptibility Changes Lead to Significant Temperature Errors in PRFS-Based MR Thermometry During Thermal Interventions. In: Magn. Reson. Med, vol. 64, (2010) pp. 1360-1372.

Soher et al. Noninvasive Temperature Mapping With MRI Using Chemical Shift Water-Fat Separation. In: Magn Reson Med, vol. 63, (2010) pp. 1238-1246.

Salomir et al.: "A Fast Method for Magnetic Field Inhomogeneity due to an Arbitrary Distribution of Bulk Susceptibility", ERT Imagerie moleculaire et fonctionnelle, CNRS/Universite de Bordeaus 2, 146 rue Leo Saignat, case 117, 33076 Bordeaux, France aus "Concepts in Magnetic Resonance Part B", Magnetic Resonance Engineering, vol. 19B (1), pp. 26-34, (2003).

Son et al. "Single-point Dixon water-fat imaging using 64-channel single-echo acquisition MRI" Concepts in Magnetic Resonance Part B: Magnetic Resonance Engineering, vol. 33B, Issue 3, pp. 152-162, published online: (2008).

Ma: "A Single-Pont Dixon Technique for Fat-Suppressed Fast 3D Gradient-Echo Imaging With a Flexible Echo Time", Journal of Magnetic Resonance Imaging vol. 27; pp. 881-890, (2008).

Li et al. High-Precision Mapping of the Magnetic Field Utilizing the Harmonic Function Mean value Property, Journal of Magnetic Resonance vol. 148 (2001) pp. 442-448.

Rieke et al. "Referenceless MR Thermometry for Monitoring Thermal Ablation in the Prostate," IEEE Trans. Med. Imaging vol. 26, No. 6 (2007) pp. 813-821.

\* cited by examiner

FIG 4

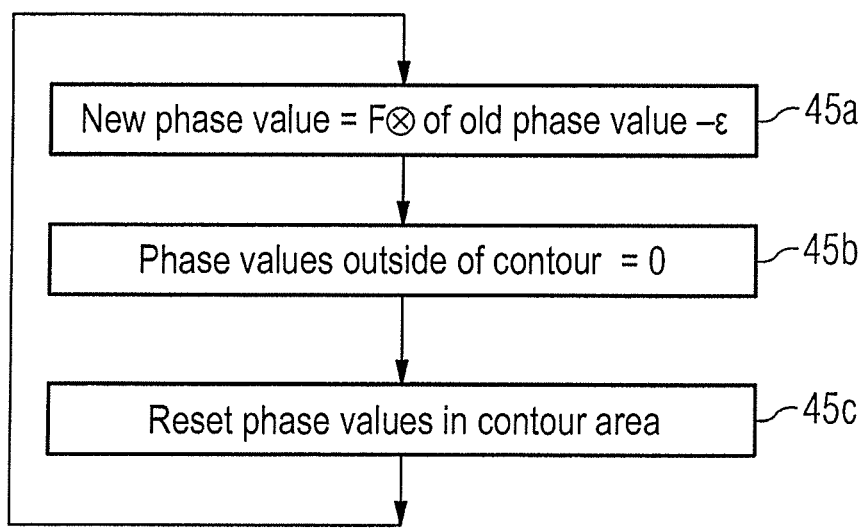

FIG 6

```
┌─────────────────────────────────────────────┐
│ New phase value = F⊗ of old phase value -ε  │─ 45a
└─────────────────────────────────────────────┘
                      ↓
┌─────────────────────────────────────────────┐
│ Phase values outside of contour = 0         │─ 45b
└─────────────────────────────────────────────┘
                      ↓
┌─────────────────────────────────────────────┐
│ Reset phase values in contour area          │─ 45c
└─────────────────────────────────────────────┘
```

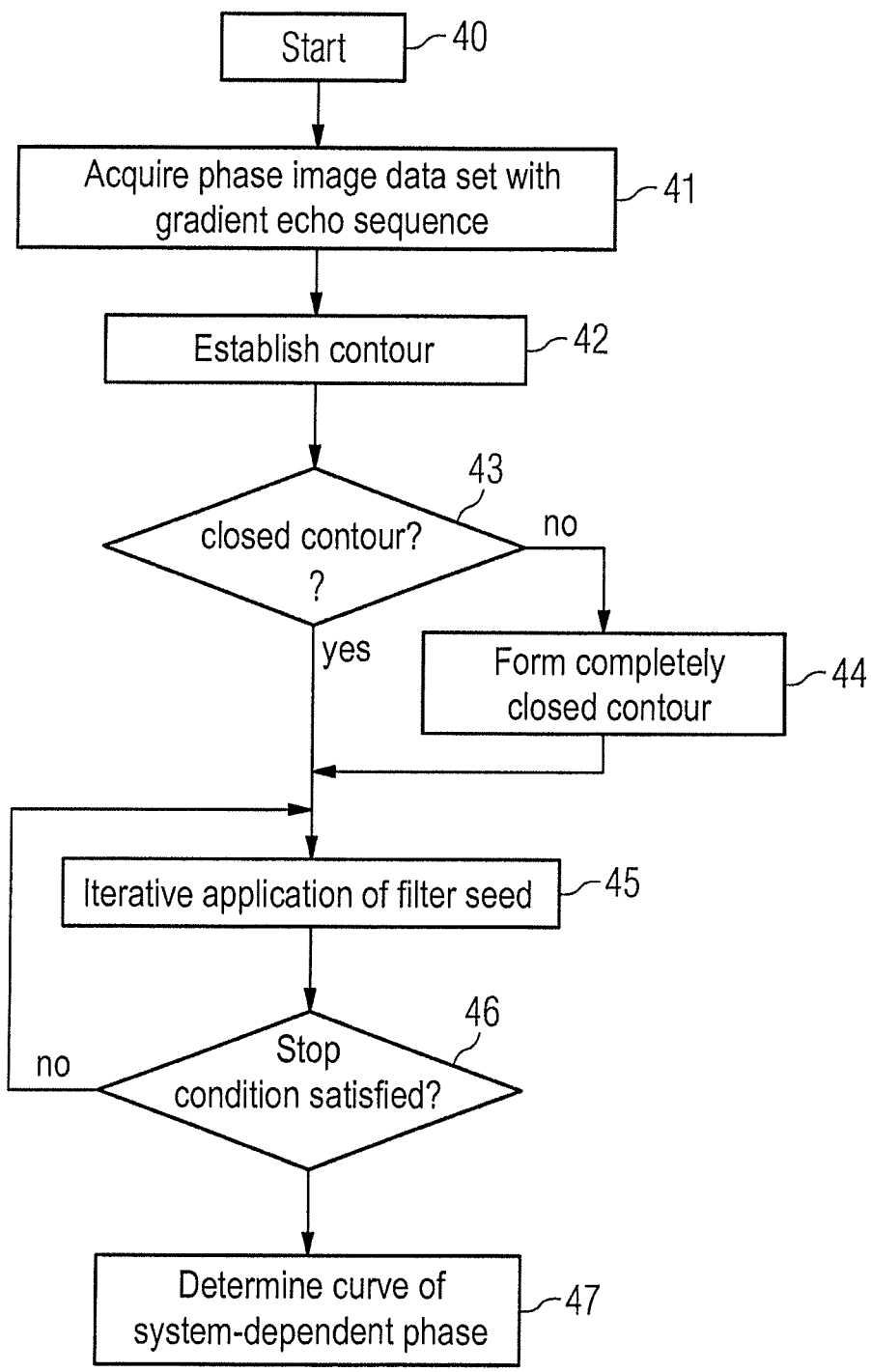

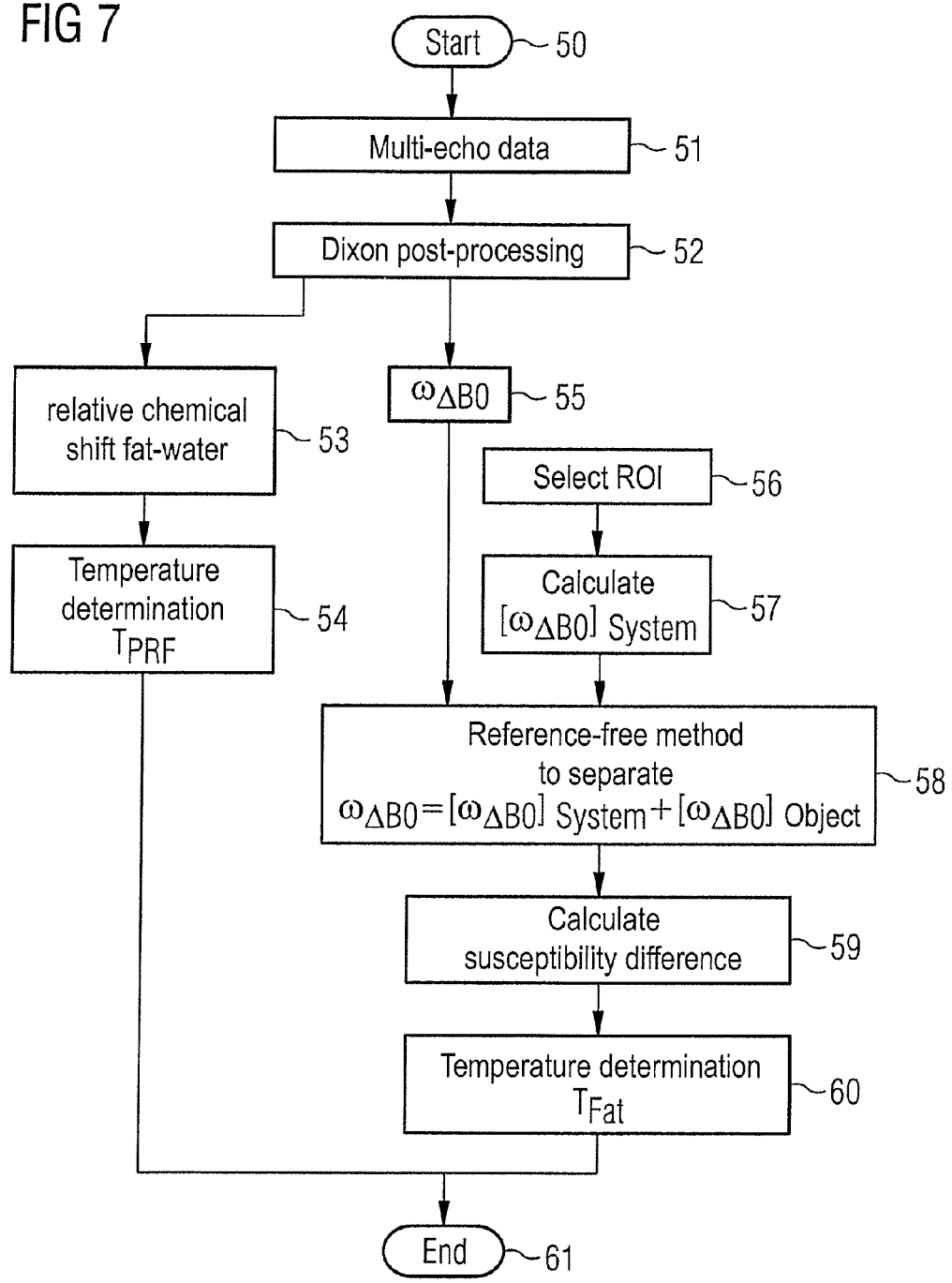

MAGNETIC RESONANCE METHOD AND SYSTEM FOR PHASE CORRECTION OF MAGNETIC RESONANCE SIGNALS ORIGINATING IN MIXED TISSUE

BACKGROUND OF THE INVENTION

1. Field of the Invention

The present invention concerns a method to separate a magnetic resonance (MR) system-dependent phase influence from a subject-dependent phase influence in phase values of an MR phase image data set, and an MR system for implementing such a method.

2. Description of the Prior Art

The phase information of a magnetic resonance signal, which describes the attitude (orientation) of the magnetization perpendicular to the $B_0$ field direction, can be used in many ways in magnetic resonance tomography (MRT). For example, the phase information contained in the MR signal can be used to separate fat and aqueous tissue, for flow measurement, in susceptibility-weighted MRT and for temperature determination. In a method known as thermotherapy, the temperature in tumor cells is increased in a targeted manner in order to kill the tumor cells or to make these sensitive to accompanying therapy measures. For example, the tissue heating can take place by focused ultrasound or with the use of lasers. In order to not destroy healthy tissue due to the increased temperature, temperature monitoring of the heated tissue is required. Certain MR parameters—such as the chemical shift, the T1 relaxation time or the diffusion constant for non-invasive temperature measurement—can be used in addition to an invasive temperature measurement with temperature probes placed in the heated tissue.

In the case of temperature monitoring based on the temperature dependency of the chemical shift (PRF), the resonance frequency altered by the temperature change is detected in an image point in an altered phase position. Only temperature changes can be shown in temperature imaging based on chemical shift, for example by taking the difference of two phase image data sets that were acquired at different temperatures. The phase image data set acquired at a known capture temperature serves as a reference data set from which the subsequent phase image data sets are subtracted. These methods operating with reference data sets have the disadvantage that movements of the examination subject between the acquisition of the two data sets, or other external interferences, lead to phase changes that are incorrectly interpreted as temperature changes. Furthermore, the $B_0$ field constancy over time and current drift in the shim coils play a role, since these also lead to phase changes in the detected signal that can likewise incorrectly be identified as temperature changes. In addition to these methods with reference image data sets, there are techniques known as reference-less (reference-free) methods in which a temperature is concluded only from the measured phase values. These methods have the disadvantage that information must exist as to how the MR system-dependent background phase varies spatially across the image. The phase position in an image point is affected not only by the frequency of the magnetization in this image point but also by system components, for example the RF receiver or the demodulator.

In DE 10 2009 058 510.9 a method is described as to how the background phase in phase values of an MR phase image data set can be determined in a simple manner without using reference data sets. In such a method, however, the acquired phase image data set contains only signals of a single tissue type. For application to tissues of multiple tissue types with different frequencies (fat and aqueous, for example), the other tissue type (most often the fat) is suppressed by either only one tissue type being excited, or in that both tissue types are excited and the signals of the one tissue type are destroyed before the signal detection, so that the suppressed tissue type no longer provides any signal contribution to the MR signal. In image points at which low tissue proportions of the unsuppressed signal are contained, the method described in DE 10 2009 058 510.9 delivers only a low signal-to-noise ratio. Moreover, it is often difficult to completely suppress the signals of the unwanted tissue portion.

A further problem is that the susceptibility in the heated fat tissue changes in the case of non-invasive temperature imaging with the use of the proton resonance frequency (PRF) method, which in turn affects the phase values in the immediate vicinity, so the temperature information is adulterated. This subject-dependent phase influence is normally not separable from the system-dependent phase influence (due to $B_0$ field fluctuations, for example).

SUMMARY OF THE INVENTION

An object of the present invention is to allow a more reliable determination of the phase value, even for mixed tissue (for example tissues with fat and water). Furthermore, for heated mixed tissues it is desirable to obtain temperature information with the use of PRF, with the temperature information not being affected by susceptibility changes of the fat due to heating.

According to a first aspect of the invention, a method is provided to separate an MR system-dependent phase influence from a subject-dependent phase influence in phase values of an MR phase image data set of the examination subject that is acquired, in which MR phase image data set two different tissue types are present with different resonances, and they each make a signal contribution, at least at a few image points. In one step the MR phase image data set is acquired and the acquired phase values are determined. These acquired phase values include the subject-dependent phase influence and the system-dependent phase influence. System-dependent phase influence means the influence on the acquired phase values that is caused by the MR system, for example due to the $B_0$ drift or by the receiver components to receive the MR signal. Subject-dependent phase influence describes internal phase effects or phase effects that are due to the examination subject, for example due to susceptibility artifacts. The system-dependent phase influence is determined by selection of a region to be examined from the examination subject shown in the MR phase image data set, by a contour around the region to be examined being selected (marked). The system-dependent phase influence in the region to be examined is subsequently calculated with the use of the selected contour, with the assumption that the spatial phase curve of the background phase corresponds to a harmonic or quasi-harmonic function. This means that the system-dependent phase influence is determined with the method that is described in detail in DE 10 2009 058 510.9. With knowledge of the system-dependent phase influence, the subject-dependent phase influence on the acquired MR phase can then be determined by subtracting the system-dependent phase influence from the acquired phase image data set. This advantageously takes place image point-by-image point, since the system-dependent phase influence for the individual image points and the acquired phase image data set exist for each image point, such that the subject-dependent phase influence can be determined for each image point. For example, with such a method it is also possible to calculate phase information in image points, which phase information comprises signal portions of tissues with different resonance frequencies.

According to a preferred embodiment, the phase image is acquired with the use of the Dixon technique in which at least two echoes of the examined tissue are acquired. The two tissue types have essentially the same phase position a first echo, while at a second echo the two tissue types have essentially opposite phase position. The acquired phase values are thereby determined with the use of the first echo, in which both tissues have the same phase position. The phase position occurring at this point in time is ideally zero. The phase values measured at this first echo are the phase values that include the system-dependent and subject-dependent phase influence. The method described in DE 10 2009 058 510.9 can then be used to separate these two phase influences.

The method can also be used in connection with temperature imaging. In a preferred embodiment, given a heated examination subject the system-dependent phase influences are subtracted from the acquired phase values in order to obtain the subject-dependent phase influences. After subtracting this system-dependent influence, the subject-dependent phase change can then be converted into a temperature change.

Since the subject-dependent phase change is in large part due to the temperature change of the susceptibility, the susceptibility to the temperature change of the tissue can be concluded from the temperature change.

The chemical shift between fat and water is advantageously calculated with the aid of the Dixon technique, wherein at least four signal echoes are acquired.

The change of the susceptibility given the heating of a tissue can also be accounted for with the aid of the subject-dependent phase influences and their determination. The relative chemical shift between fat and water, which is explicitly temperature-dependent, is calculated with the Dixon technique over the additional echoes. The relative chemical shift between fat and water is determined in the Dixon technique. Since fat has an essentially negligible temperature dependency of the chemical shift in comparison to water, the relative shift between fat and water allows the direct measurement of the temperature. Given normal body temperature, the chemical shift between fat and water is approximately 3.5 ppm. Any additional change can thus be ascribed to the chemical shift of the water that is altered due to temperature. $d\sigma_{fat}/dT=0.00018$ ppm/° C. (which is negligible) and $d\sigma_{Water}/dT=0.098$ ppm/° C. hereby apply. It is therefore possible to calculate the phase influence due only to temperature. If the system-dependent phase is now subtracted from the measured phase, the subject-dependent phase is obtained. This is essentially determined by the susceptibility changes of the fat. With the use of the known temperature dependency of the susceptibility, it is then possible to conclude the temperature change of the fat—the temperature change of the fat—from the subject-dependent phase change. This leads to additional temperature information about the heated tissue since the heated fat takes on the same temperature as the other tissue in the surroundings that do not consist of fat.

In a preferred embodiment, the variables $\omega_2$, $r_1$, $(T_2^*)1$ and $(T_2^*)2$ and $\omega_{AB0}$ are calculated with the use of the four echoes. $\omega_2$ is hereby the frequency difference between the two tissue types, $R_1$ corresponds to the proportion of fat in an image point, $(T_2^*)1$ and $(T_2^*)2$ are the $T_2^*$ times of the first and second tissue, respectively, and $\omega_{AB0}$ is the frequency change corresponding to the measured phase value, which frequency change contains the subject-dependent and system-dependent phase influence.

Unheated phase image points are advantageously used in order to determine the system-dependent phase influence on the measured phase values of the phase image data set in the heated region.

The invention furthermore concerns a magnetic resonance system with an image acquisition unit to acquire the MR phase image data set, and a computer that—as described above—is in the position to separate the system-dependent phase influence from the subject-dependent phase influence.

BRIEF DESCRIPTION OF THE DRAWINGS

FIG. 4 is a portion of a phase image data set with a flat contour, and the application of a filter seed from the phase image data set to separate the system-dependent phase and subject-dependent phase.

FIG. 5 is a flow chart with the primary steps to calculate the spatial curve of the system-dependent phase.

FIG. 6 is a flow chart that shows the method steps described during the application of the filter kernel in more detail.

FIG. 7 is a flow chart given the application of the invention to heated tissue, with separate determination of a temperature change via the chemical shift between fat and water and via the subject-dependent susceptibility change.

DESCRIPTION OF THE PREFERRED EMBODIMENTS

Figure 1:
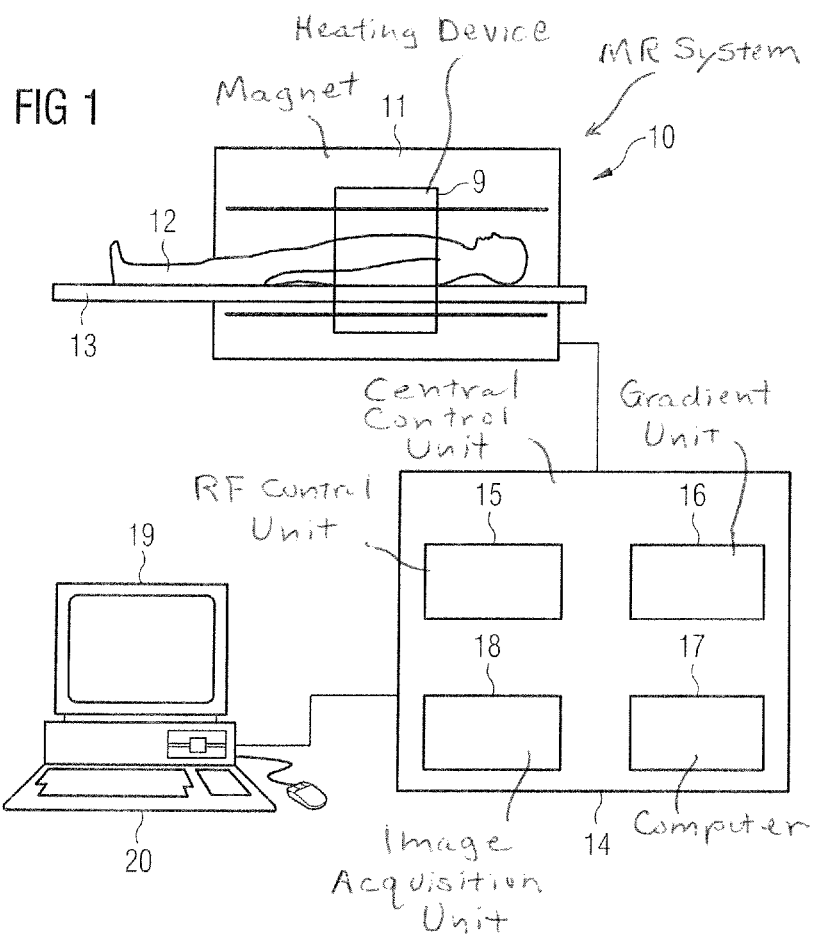
FIG. 1 schematically shows an MR system with which the system-dependent phase influence can be separated from the subject-dependent phase influence.

An MR system 10 is schematically shown in FIG. 1 with which the system-dependent phase information can be separated from the subject-dependent phase information and with which—given heating of an examined tissue—in addition to the temperature information, the susceptibility change of the fat upon heating can be calculated, for example.

The MR system has a magnet 11 to generate a $B_0$ field into which an examined person 12 arranged on a bed 13 can be inserted. The shown MR system can be used, for example, in combination with a thermotherapy in which individual regions of the examined body are heated (for example with ultrasound) in order to destroy tumor tissue located in the heated region. The temperature development in the shown tissue can be non-invasively checked in multiple dimensions with the acquisition of MR phase images of a gradient echo sequence and the presentation of phase images. The MR system has a central control unit 14 with which the control of the MR system is possible. Since the basic functionality to generate MR images is known to the man skilled in the art, only a few system components are schematically discussed in the following. An RF control unit 15 controls the radiation of RF pulses into the examination subject into the examination subject; a gradient unit 16 controls the switching of the gradients required for spatial coding. An image acquisition unit 18 controls the time sequence of the radiation of the RF pulses and the gradient switchings, and the detection of the MR signal, depending on the selected imaging sequence. As is explained in detail in the following, a computer 17 can then calculate the background phase (which accounts for the system-dependent and subject-dependent phase influence) from the calculated MR phase image data sets. The generated MR image data can be presented at a display unit 19, wherein a flat contour in a phase image data set around a partial region in which information about the background phase is desired can be drawn via an input unit 20, for example. The subsequently described method can be used in non-invasive temperature imaging; however, the calculation of the background phase is also important for other fields of application, for example in susceptibility-weighted MRT, in flow measurement, in the determination of the fat content in a tissue etc. The device to heat the examined tissue is schematically shown with the reference character 9.

Figure 2:
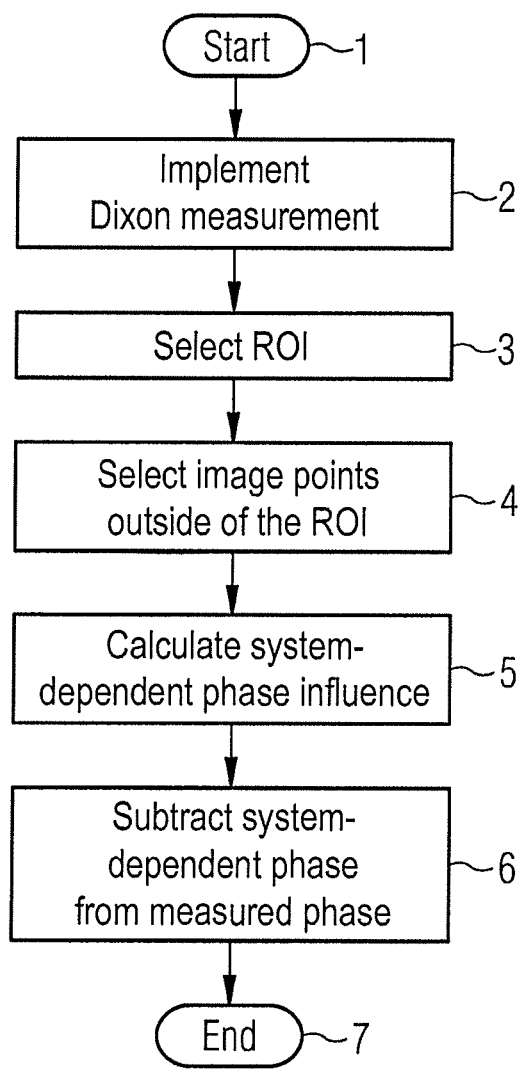
FIG. 2 is a flow chart with the steps to separate the system-dependent phase information from the subject-dependent phase information.

The basic steps to calculate the system-dependent and subject-dependent phase influence are shown in FIG. 2. The method starts in Step 1. In Step 2 a Dixon measurement is implemented in order to generate a phase image data set in which the phase values of the first echo (in which the examined tissue portions have the same phase position) is [sic] used. These phase values include the subject-dependent and system-dependent phase influence. In the further Steps 3 through 7, the two influences are now separated from one another. For this, in Step 3 a region is selected in which the two items of phase information should be separated, for example. This region is also called a Region of Interest (RoI). In a further Step 4, image points outside of the RoI are selected, and in Step 5 the system-dependent phase influence is calculated as is described in detail in DE 10 2009 058 510.9. If the system-dependent phase influence on the phase values of the image data set is known after Step 5, in Step 6 the system-dependent phase influence can be subtracted from the measured phases, whereby the subject-dependent phase influence is obtained according to Step 6. The method ends in Step 7. The method described in DE 10 2009 058 510.9 is explained again briefly in the following with reference to FIGS. 3 through 6.

Figure 3:
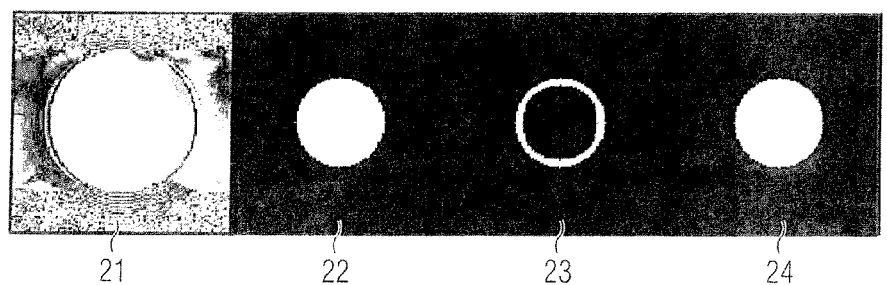
FIG. 3 shows a phase image of an examination subject as well as a region to be examined for which the background phase should be determined.

A phase image data set 21 of an examination subject is shown at the left image edge in FIG. 3. The phase values from −180° to +180° (shown in grayscale values) have a certain phase curve in the examination subject. For example, it if is now assumed that the inside of the examination subject should be heated and the temperature should be determined non-invasively with the aid of the MR phase images, the user can (as shown in image 22) mark an (advantageously circular) region in which the temperature information should be determined.

With regard to FIG. 5 this means that, after the start of the method in Step 40, a phase image data set is acquired in which the fat signals are not suppressed, but rather in which phase values are included so that a phase image data set results as is shown in image 21 of FIG. 2, for example (step 41). In a next Step 42, an operator can then establish a contour around a partial region (ROI=Region of Interest; image 22) of the phase image data set, for example as is shown in image 23 of FIG. 2. This contour is a flat contour and is at least one image point in width. This contour is advantageously placed in tissue with homogeneous susceptibility and in tissue that is not heated. With the use of the phase values in the image points in the flat contour, and with the aid of a filter seed, the phase values can now be calculated in the region within the contour (i.e. in the partial region).

In Step 43 it is checked whether the drawn contour is a closed contour or an unclosed contour. In the event that the drawn contour is a contour that is not completely closed, in Step 44 a completely closed contour is formed. If a closed contour is now present, in Step 45 a filter seed is then iteratively applied to the phase image data set.

The preferred filter kernel F is shown in FIG. 4. The phase values within the contour can now be calculated with this filter kernel. A partial region of an image with multiple image points is shown enlarged in the left portion of FIG. 4, wherein the contour 31 has a width of two image points and is represented by the two lines 32 and 33. The steps used in the iterative application of the filter kernel are shown in detail in FIG. 6. In order to calculate a phase value in the partial region that is enclosed by the contour 31 and that is labeled with reference character 34 in FIG. 4 (for example the image points c3, c4, d2, d3 and d4), an aliasing of the phase values takes place with the filter kernel F. Since this aliasing in the image region can be implemented in the image region, it corresponds to a simple multiplication of the phase values with the filter kernel. For example, the following calculation is executed to calculate the phase value in the image point c3 with the filter seed shown in FIG. 4: ¼×phase value of b3+¼×phase value of c4+¼×phase value of d3+¼×phase value of c2. In the first application of the filter kernel, the phase values in the partial region 34 are set to zero and the phase values in the flat contour 31 contain the measured phase values. After this multiplication with the filter kernel, as shown in Step 45a of FIG. 5 the constant ε is additionally subtracted that—as mentioned above—describes the deviation of the phase curve from a harmonic function. In the next iteration step 45b, the phase values outside of the contour—i.e. the phase values in the image points a1, a2 and b1 in the example of FIG. 4—are set to zero. In Step 45c of the iteration the phase values in the flat contour are then again reset to their originally measured values before the multiplication with the filter seed before Step 45a can be repeated. The calculation of the phase values inside of the contour (i.e. in the partial region 34) can take place until the phase position calculated with the aid of the filter kernel no longer spatially changes (or changes only slightly) between two iteration steps. With regard to FIG. 5, this means that in Step 46 it is checked whether a stop condition to terminate the iteration is satisfied or not. This stop condition can depend on a count of the implemented iterations that in turn depends on the size of the partial region, or the stop condition can be set such that the iteration is terminated if the spatial phase curve no longer significantly changes from one iteration step to the next. A background phase of such a design is shown as an example in image 24, which background phase was calculated in the examination region of the ROI of image 22.

The constant ε enables the three-dimensional Laplace condition to be applied in two dimensions, for example as in the regions shown in FIG. 3. The smaller the ROI drawn in image 22, the better this approximation. Before the heating, in the given ROI an optimal value for ε can be determined that minimizes the standard deviation of the calculated temperature. Returning to FIG. 5, this means that—in the event that the stop condition is satisfied in Step 46—the system-dependent phase curve is determined in Step 46, as it is shown in image 24 of FIG. 3. In addition to the determination in the image, ε can also be calculated as explained above. For further details regarding the determination of the system-dependent phase influence, refer to DE 10 2009 058 510.9. As is also described there, the contour does not need to be closed.

Because the system-dependent phase influence in the phase values of the phase image data set has now been calculated as described above, the subject-dependent phase influence results after subtracting this system-dependent phase influence from the measured phase values.

In the following the Dixon technique is discussed briefly with two or more echoes. In the Dixon technique it is assumed that the signal in an image point contains two tissue types, namely fat and water. The fat proportion is r while the water proportion is thus (1−r), wherein r varies between 0 and 1. Each tissue type has its own resonance frequency $\omega_{Fat}$ and $\omega_{Water}$. Due to the different resonance frequencies, the dephasing and rephasing of the complete signal depends on the echo time. In addition to the parameters of the spin system (such as r, $\omega_{Fat}$ and $\omega_{Water}$), the signal that was acquired in the phase image data set also still depends on system-dependent phase influences (for example local $B_0$ field inhomogeneities). This leads to a further phase change of the signal with a frequency $\omega_{\Delta B0}$. In the present case this phase modulation includes the system-dependent phase influence and subject-dependent phase influence, since which effect the measured phase is dependent upon is not known from said measured phase. The signal in a voxel with fat and water at echo time $T_N$ now reads as follows:

Error! Objects cannot be created from editing field codes. (1)

wherein B is the complex signal value at the echo point in time 0 and $n_n$ is the noise in the measurement of the n-th echo. The $T_2^*$ decay is hereby ignored in the standard Dixon technique. In the event that the acquisition takes place with multiple coils, the signal of the n-th coil reads as follows:

Error! Objects cannot be created from editing field codes. Error! Objects cannot be created from editing field codes. (2)

wherein the indices m, n indicate the acquisition coil or, respectively, the echo time. The $T_2^*$ decay at short echo times is ignored in standard Dixon techniques. However, larger echo times are used in the PRF method for temperature calculation, such that the $T_2^*$ times can no longer be ignored. This leads to an additional unknown that must be calculated in the event that the method described here for the separation of system-dependent phase effects and subject-dependent phase effects should be used in temperature imaging. A flow chart is now shown in FIG. 7 in which the temperature change can be determined by an altered chemical shift given heated tissue, and a susceptibility change can be concluded from the subject-dependent phase curve or, respectively, a variable which reflects the temperature increase in the fat can be calculated via the known temperature dependency of the susceptibility in fat.

The method starts in Step 50, and in Step 51 the multi-echo data are acquired with four echoes, for example. The calculation of $\omega_{\Delta B0}$, $\omega_2$, $r_1$, $(T_2^*)1$ and $(T_2^*)2$ follows in Step 52 via Dixon post-processing. This calculation of these variables with the Dixon technique is known to those skilled in the art, such that it need not be described in detail herein. Multiple methods for calculation are known (Step 52).

It is now possible to arrive at temperature information with the PRF method. For this, in Step 53 the relative chemical shift between fat and water is determined, i.e. $\omega_2$ with $\omega_{Fat-Water}=\omega_2$. Since fat has an essentially negligible temperature dependency of the chemical shift, and the temperature dependency of the chemical shift of water is known at 0.0098 ppm/° C., in Step 54 a temperature change can be concluded from the chemical shift. At normal body temperature the chemical shift amounts to 3.5 ppm, for example. Upon heating the tissue, this variable varies due to the temperature dependency of the chemical shift of water, and the temperature change can then be concluded (Step 54) from the altered chemical shift between fat and water.

Temperature information can be obtained with the steps shown in the right branch of FIG. 7. The fact that the heating alters the susceptibility of fat but not of water is hereby utilized. The variation of the susceptibility of fat thus also modifies the subject-dependent phase influence. The variable $\omega_{\Delta B0}$ that includes the subject-dependent phase influence and system-dependent phase influence follows (Step 55) from the Dixon post-processing in Step 52. If an ROI is now selected in Step 56 and the system-dependent phase influence is calculated as described in connection with FIG. 2-6 (Step 57), the subject-dependent phase influence can be determined in Step 58 via the measured phase and the subtraction of the system-dependent phase. In Step 59 the local susceptibility difference can be calculated from this as is described by Rares et al. in "Concepts in Magnetic Resonance Part B (Magnetic Resonance Engineering)", Vol. 19B(1) 26-34, 2003, for example. A temperature in the subject—here the fat—can be concluded from the subject-dependent phase influence with calculation of the susceptibility differences (Step 60).

The temperature change can be calculated from the subject-dependent phase change via the known temperature dependency of the susceptibility $\chi$.

The temperature dependency of $\chi_{Fat}$ is:

Error! Objects cannot be created from editing field codes.

This lies within the same order of magnitude as the temperature dependency of the chemical shift a of the water protons, which is used in the PRF method:

Error! Objects cannot be created from editing field codes.

In summary, this means that the relative chemical shift between fat and water can be explicitly calculated or, respectively, measured via the additional measured echoes in Step 51. The temperature-dependent phase change can therefore be calculated. Furthermore, the combined system-dependent and subject-dependent phase influence is obtained, which can be separated as was described in connection with FIG. 2 through 6. After separating these two effects, the subject-dependent phase influence can be determined. In the case of heating, this is essentially determined by the susceptibility change of the fat. However, this temperature-dependent change of the susceptibility offers an additional indicator for the temperature change in the heated tissue that can be used in addition to the PRF method. The method ends in Step 61.

In summary, the present invention enables the calculation of susceptibility changes in fat given heated tissue, and the calculation of susceptibility-corrected temperature information with the PRF method.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to separate a magnetic resonance (MR) system-dependent phase influence from a subject-dependent phase influence in phase values of an MR phase image data set of an examination subject, comprising the steps of:

operating an MR data acquisition unit to acquire MR phase image data, comprising phase values, from an examination subject in the MR data acquisition unit, wherein two different tissue types with respectively different resonance frequencies supply a signal contribution to at least some phase values in said MR phase image data set, said phase values each comprising a subject-dependent phase value contribution to the respective phase value that is produced by the examination subject and an MR system-dependent phase value contribution to said respective phase value that is produced by the physical attributes of said MR data acquisition unit;

supplying said MR phase image data set to a computerized processor and, in said processor, automatically determining said MR system-dependent phase value contribution by selecting a region to be examined that is represented within the MR phase image data set by designating a contour around said region, and calculating the MR system-dependent phase value contribution in said region using the selected contour and assuming that a spatial curve of background phase corresponds to a harmonic or quasi-harmonic function; and in said processor, subtracting the determined MR system-dependent phase value contribution from the acquired MR phase image data set to determine the subject-dependent phase value contribution, and making the subject-dependent phase value contribution available in electronic form at an output of said processor.

2. A method as claimed in claim 1, comprising operating said MR data acquisition unit using a Dixon technique to acquire said MR phase image data set, by acquiring at least two echoes from the examination subject following excitation of said two different tissue types, said two different tissue types having a substantially same phase position in a first of said at least two echoes and a substantially opposite phase position in a second of said at least two echoes, and determining said phase image data set using said first echo.

3. A method as claimed in claim 1, wherein said two different tissue types are fat and water.

4. A method as claimed in claim 1, comprising heating at least said region of the examination subject and determining a temperature change of the heated region of the examination subject from said subject-dependent phase value contribution.

5. A method as claimed in claim 4 wherein said two different tissue types are fat and water, and determining a chemical shift between said fat and said water using a Dixon technique in which at least four echoes are acquired following excitation of said fat and water.

6. A method as claimed in claim 5 wherein said subject-dependent phase influence is substantially due to changes in susceptibility of heated tissue in said heated region, and calculating said changes in susceptibility using said four echoes and determining a temperature of the heated region of the examination subject from said changes in susceptibility.

7. A method as claimed in claim 6, comprising calculating variables $\omega_2$, $r_1$, $(T_2^*)1$ and $(T_2^*)2$ and $\omega_{\Delta B0}$ using the four echoes, wherein $\omega_2$ is a frequency difference between the two tissue types, $r_1$ corresponds to a proportion of fat in an image point, $(T_2^*)1$ and $(T_2^*)2$ are the T2* times of the first and second tissue types, and $\omega_{\Delta B0}$ is a frequency change corresponding to the measured phase value, said frequency change containing the subject-dependent and system-dependent phase value contribution.

8. A method as claimed in claim 4 comprising using image points that are unheated to determine said system-dependent phase influence on the phase values of the MR phase image data set in the heated region.

9. A magnetic resonance (MR) system comprising:

an MR data acquisition unit;

a control unit configured to operate said MR data acquisition unit to acquire MR phase image data, comprising phase values, from an examination subject in the MR data acquisition unit, wherein two different tissue types with respectively different resonance frequencies supply a signal contribution to at least some phase values in said MR phase image data set, said phase values comprising a subject-dependent phase value contribution to the respective phase value that is produced by the examination subject and an MR system-dependent phase value contribution to said respective phase value that is produced by the physical attributes of said MR data acquisition unit;

a computerized processor configured to automatically determine said MR system-dependent phase value contribution by selecting a region to be examined that is represented within the MR phase image data set by designating a contour around said region, and calculating the MR system-dependent phase value contribution in said region using the selected contour and assuming that a spatial curve of background phase corresponds to a harmonic or quasi-harmonic function; and said processor being configured to subtract the determined system-dependent phase value contribution from the acquired MR phase image data set to determine the subject-dependent phase value contribution, and making the subject-dependent phase value contribution available in electronic form at an output of said processor.

* * * * *